United States Patent [19]
Platzek et al.

[11] Patent Number: 5,747,000
[45] Date of Patent: May 5, 1998

[54] USE OF MACROCYCLIC METAL COMPLEXES AS TEMPERATURE SENSORS

[75] Inventors: Johannes Platzek; Bernd Radüchel; Ulrich Niedballa; Hanns-Joachim Weinmann; Hans Bauer; Klaus Roth, all of Berlin, Germany

[73] Assignee: Schering Aktiengesellschaft, Berlin, Germany

[21] Appl. No.: 549,803

[22] PCT Filed: Apr. 29, 1994

[86] PCT No.: PCT/EP94/01376

§ 371 Date: Mar. 8, 1996

§ 102(e) Date: Mar. 8, 1996

[87] PCT Pub. No.: WO94/27977

PCT Pub. Date: Dec. 8, 1994

[30] Foreign Application Priority Data

May 28, 1993 [DE] Germany ............ 43 18 369.7

[51] Int. Cl.$^6$ .................................. A61B 5/055
[52] U.S. Cl. .................. 424/9.363; 534/16; 540/465; 540/474; 436/173; 524/184; 524/836
[58] Field of Search .................. 424/9.363; 540/474, 540/465; 436/173; 128/653.4, 654; 514/184, 836; 534/16

[56] References Cited

U.S. PATENT DOCUMENTS

| | | | |
|---|---|---|---|
| 4,558,279 | 12/1985 | Ackerman et al. | 324/315 |
| 4,647,447 | 3/1987 | Gries et al. | 424/9 |
| 4,767,611 | 8/1988 | Gordon | 424/9 |
| 4,885,363 | 12/1989 | Tweedle et al. | 540/465 |
| 5,011,925 | 4/1991 | Rajagopalan et al. | 544/58.1 |
| 5,250,285 | 10/1993 | Lauffer et al. | 424/9 |
| 5,316,757 | 5/1994 | Sherry et al. | 424/9.363 |
| 5,322,681 | 6/1994 | Klaveness | 424/9.363 |
| 5,358,704 | 10/1994 | Desreux et al. | 424/9.363 |
| 5,362,478 | 11/1994 | Desai et al. | 424/9 |
| 5,374,416 | 12/1994 | Rousseaux et al. | 424/2 |
| 5,397,562 | 3/1995 | Mason et al. | 424/9 |
| 5,417,960 | 5/1995 | Schaefer et al. | 424/9.363 |
| 5,490,840 | 2/1996 | Uzgiris et al. | 604/22 |
| 5,512,268 | 4/1996 | Grinstaff et al. | 424/9.322 |

*Primary Examiner*—Gary E. Hollinden
*Attorney, Agent, or Firm*—Millen, White, Zelano, & Branigan, P.C.

[57] ABSTRACT

The invention relates to the use of macrocyclic metal complexes that consist of a complexing agent of formula I and at least one metal ion of an element of atomic numbers 21–29, 42, 44 or 57–70

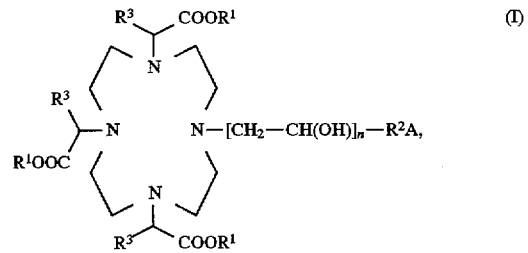

in which n, $R^1$, $R^2$, $R^3$ and A are as set forth in the specification, are useful as temperature sensors.

27 Claims, 2 Drawing Sheets

USE OF MACROCYCLIC METAL COMPLEXES AS TEMPERATURE SENSORS

This application is a 371 of PCT/EP94/01376 filed Apr. 29, 1994, published as WO94/27977 Dec. 8, 1994.

The invention relates to the object characterized in the claims, i.e., the use of macrocyclic metal complexes as temperature sensors in NMR [nuclear magnetic resonance] diagnosis.

With the aid of modern diagnostic methods, it is possible to depict extremely small morphological structures at a resolution that comes close to that of the tissue sections of anatomy textbooks. This enormously high resolution is achieved, on the one hand, by constantly improved hardware, but, on the other hand, also with the aid of contrast media. With the various known methods, such as ultrasonic diagnosis, diagnostic radiology, nuclear medicine and even nuclear spin tomography, however, it is not possible to obtain information on the metabolic-physiological state of a tissue in the living organism. For a more exact diagnosis and especially for planning and monitoring the course of therapeutic intervention, however, such knowledge is of considerable importance, since an optimum treatment can be successful only if a statement on its effect is possible early on.

It is known that an important factor in metabolic-physiological activity is temperature. The determination of this tissue temperature provides important information on the function and state of the cells, so that it is desirable to locate sites that have temperatures which deviate from normal body temperature. This makes it possible to identify pathologically altered tissue and optionally to perform treatment.

Body temperature is a product of the activity of energy metabolism and is subject to varied influences.

Blood flow represents a significant value of influence on local tissue temperature; via blood flow the body attempts to offset temperature drops that occur constantly [K. Brück, Heat Balance and Temperature Regulation, in: Physiologie des Menschen [Human Physiology], R. F. Schmidt, G. Thews (Editors), Springer Verlag, 23rd Edition, 1987]. The measurement of temperature therefore offers a way to delimit local increased blood circulation (e.g., in the case of inflammations) or restricted blood circulation (e.g., in ischemic regions) in a tissue against its healthy environs.

In the case of hyperthermia treatment for tumor diseases, the measurement of tissue temperature is an important parameter for monitoring the course of the radiation. At the moment, only invasive methods can be used for this purpose [P. Fessenden, Direct Temperature Measurement, in: Hyperthermia in Cancer Treatment, Cancer Research, 44 (Suppl.), 4703s–4709s, 1984].

It is now known that the chemical shift of signals in in vitro NMR spectroscopy is also a function of temperature. This influence is caused by intermolecular and intramolecular interactions. In high-resolution NMR spectroscopy, intermolecular interactions, e.g., with the solvent, quite decisively determine the chemical shift. The solvation of the molecule under study, including intermolecular aggregation and hydrogen bridging, depends greatly on temperature. Hydrogen bridge bonds are broken at elevated temperatures and thus change the chemical environment of the atomic nuclei. In the case of substances that form strong intermolecular hydrogen bridge bonds, the temperature coefficient of the chemical shift is especially large. With the aid of calibration curves, temperature can then be determined exactly from the chemical shift that is measured empirically.

In this case, particularly the aliphatic alcohols, which tend toward strong hydrogen bridge bonds, have proven to be of value:

Methanol $CH_3OH$: $T=409.0-36.54\Delta\delta-21.85(\Delta\delta)^2$

Ethylene glycol $HOCH_2$—$CH_2OH$: $T=466.5-102.00\Delta\delta$ in which $\Delta\delta$ is the difference in the chemical shifts between the OH and CH signals in ppm and T is absolute temperature in K [R. Duerst, A. Merbach, Rev. Sci. Instrum. 36, 1896 (1965)].

The change in the chemical shift with temperature due to intermolecular interaction is by no means limited to the proton; rather it is a general property of all magnetically active atomic nuclei, so that a whole series of temperature standards have been proposed in the literature.

| Standard Substance | Atomic Nuclei | Temp.-gradient ppm/K | Literature* |
|---|---|---|---|
| Methanol | proton | 0.015 | (1) |
| ethylene glycol | proton | 0.016 | (1),(9) |
| $CH_2I_2$/cyclooctane | carbon | 0.07 | (2) |
| $CH_3I$/tetramethylsilane | carbon | 0.02 | (2) |
| MgATP complex | phosphorus | 0.012 | (3),(9) |
| $K_3Co(CN)_6$ | cobalt | 1.504 | (4),(9) |
| Co-acetylacetonate | cobalt | 3.153 | (4),(9) |
| $(CBrF_2)_2/CClF2)_2$ | fluorine | 0.0071 | (5) |
| $CFCl_3/CBr_2F_2$ | fluorine | 0.0012 | (5) |
| perfluorotributylamine | fluorine | 0.0003 | (6) |
| $(CH_3)_2TlNO_3$ | thallium | 0.44 | (7) |
| methanol | deuterium | 0.015 | (8) |

*See bibliographic index

Further, a $^{13}C$—NMR thermometer has been proposed which is based on the change in the complexing constants between shifting reagent $Yb(fod)_3$ and acetone [H. J. Schneider, W. Freitag, M. Schommer, J. Magn. Reson. 18, 393 (1973)]. This process can be used only in organic solvents, however.

In virtually all organic compounds, the influence of intramolecular interactions on the chemical shift is too small to be able to use it for temperature measurements. In the literature, only one example of this type is described, in which the intramolecular rotational barrier in furfural and the associated linear changes in the $^{13}C$—NMR spectrum were used for temperature measurement [S. Combrisson, T. Prange, J. Magn. Reson. 19, 108 (1973)]. This process is suitable, however, only in a very narrow temperature range, and this measurement range depends greatly on the magnetic measuring field strength used.

Use of these methods for in vivo temperature measurement of body tissues is as yet unsuccessful, however, for various reasons. For instance, most of the compounds described in the literature cannot be mixed with water, or are soluble only in nonpolar organic solvents, such as chloroform. Thus, use in intact biological systems is virtually impossible. Although the introduction of a pure perfluorotributylamine bubble into a rabbit's eye and subsequent temperature measurement are possible [B. A. Berkowitz, J. T. Handa, C. A. Wilson, NMR in Biomedicine 5, 65 (1992)], this process is highly invasive and cannot be transferred to other organs. Some of the water-soluble compounds such as methanol, ethylene glycol, $K_3Co(CN)_6$ and thallium salts must be excluded from the start because of their high toxicity. Of the substances described, theoretically only the MgATP complex is suitable as an endogenous temperature sensor. Since the relative MgATP concentration in cytosol is small (around 10 mmol/kg) and cannot be increased by external administration because of the creatinine-kinase equilibrium and since in addition the phosphorus nuclei are insensitive and the chemical shift is also heavily dependent on the ionic strength and the pH of the medium, a precise temperature determination with $^{31}P$—NMR measurements of MgATP within a reasonable time is not possible. Thus, all temperature sensors that are described in the literature are unsuitable for an in vivo temperature measurement in routine clinical diagnosis.

The object of this invention was therefore to find suitable compounds for in vivo temperature measurement by means of NMR spectroscopy.

These compounds must meet the following requirements:

a) They must react to a change of temperature with a changed resonance frequency in the NMR spectrum, b) They must exhibit a pronounced chemical shift per degree of temperature change, c) They must exhibit pharmacokinetics that is suitable for diagnostic applications, d) They must exhibit a concentration in the target tissues that is high enough for measuring, e) They must exhibit good compatibility and low toxicity, f) They must exhibit metabolic stability, g) They must exhibit high chemical stability and long shelf life and h) They must exhibit good water-solubility.

It has now been found that macrocyclic metal complexes that consist of at least one metal ion of an element of atomic numbers 21–29, 42, 44 or 57–70 and a complexing agent of general formula I in which n means the numbers 0 or 1,

$R^1$ independently of one another, stand for a hydrogen atom or a metal ion equivalent, $R^3$ stands for a hydrogen atom, a straight-chain or branched $C_1$–$C_{10}$ alkyl group, which is optionally substituted by 1–5 $C_1$–$C_6$ alkoxy groups, hydroxy-$C_1$–$C_6$ alkyl groups and/or hydroxy groups, $R^2$ means a straight-chain or branched $C_1$–$C_{10}$ alkylene group, which optionally is interrupted by 1 to 5 oxygen atoms and/or carbonyl groups and/or optionally is substituted by 1 to 5 hydroxy groups, $C_1$–$C_6$ alkoxy-$C_1$–$C_6$ alkyl groups, —$OR^4$, —CO—$NR^5R^6$, —$NR^5R^6$ and/or —$NR^5$—CO—$R^6$ radicals, in which $R^4$ stands for a straight-chain or branched $C_1$–$C_4$ alkyl radical and $R^5$, $R^6$, independently of one another, have the meaning of $R^3$, and A stands for a hydrogen atom or a second macrocyclic radical of general formula II, in which n, $R^1$ and $R^3$ have the indicated meanings, where free carboxylic acid groups that are not required for complexing the metal ions are present optionally as a salt of an inorganic or organic base or amino acid and/or as an ester or amide and at least two radicals $R^1$ stand for a metal ion equivalent, are suitable as temperature sensors in NMR diagnosis.

Preferred are compounds in which $R^3$ stands for a hydrogen atom and $R^2$—A stands for a —$CH_2CH_2OCH_3$, —$CH_2CH_2O$—$C(CH_3)_3$, —$CH_2$—$CH(OH)$—$CH_2OCH_3$, —$CH_2CH(OH)$—$CH_2O$—$CH(CH_3)_2$, —$CH_2$—$CH(OH)$—$CH_2O$—$C(CH_3)_3$, —$CH_2$—$CH(OH)$—$CH_3$, —CH$(CH_2OCH_3)_2$, —$CH(CH_2OCH_3)$—$CH(OH)CH_2OH$, —$CH_2$—$CH_2$—NH—$CH_3$, —$CH_2$—$CH_2$—$N(CH_3)_2$, —$CH_2$—CO—$N(CH_3)_2$, —$CH_2$—$CH_2$—O—$CH_2$—$CH_2$—O—$CH_3$, or —$C(CH_2OCH_3)_3$ group.

Especially preferred from this group are radicals $R^2$—A, such as, e.g., —$CH_2CH_2OCH_3$—, —$CH_2CH_2O$—$C(CH_3)_3$, since the latter exhibit a smaller line width and therefore the change of the chemical shift can be determined more precisely.

Surprisingly enough, the changes in the chemical shifts of the above-mentioned complex compounds in the case of small concentrations, as are used for in vivo applications, are essentially intramolecular in origin and thus are independent of outside influences, such as ionic strength, pH, and oxygen partial pressure, i.e., the dependence of the chemical shift on temperature is based only on the interaction between a central ion and the atomic nuclei present in the ligand.

It is further surprising that this chemical shift, which is caused by intramolecular interaction, can be used for in vivo temperature measurement.

The temperature gradients depend on the measured atomic nuclei, the chemical structure of the ligand, and the central ion.

As central atoms, paramagnetic metal ions, especially those of the lanthanoid elements, are especially suitable.

It has been found, surprisingly enough, that the temperature effect on the chemical shift of the signals caused by the complexes does not move in the same direction for all complexes. Thus, e.g., the methoxy group signal of the europium complex (produced according to Example 6h) is shifted toward a low field and that of the corresponding praseodymium complex (produced according to Example 6c) is shifted toward a higher field, i.e, the praseodymium complex exhibits a positive temperature gradient, while the europium complex shows a negative temperature gradient. Thus, the possibility arises of considerably increasing the precision of the temperature measurement by mixing the two complexes in the diagnostic tools.

Figure 1:
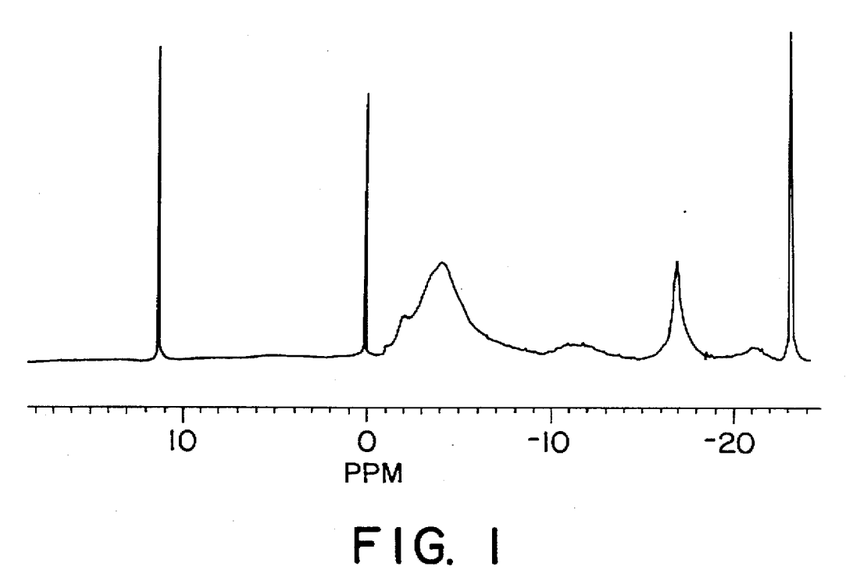
FIG. 1 shows a superposition of the in vitro spectra of europium and praseodymium complexes in $D_2O$.

FIG. 1 shows a superposition of the in vitro spectra of the above-mentioned europium and praseodymium complexes in $D_2O$ that are recorded at room temperature. The singlet at −23 ppm corresponds to the methoxy group of the praseodymium complex, and the singlet at 11.2 ppm corresponds to the methoxy group of the europium complex. The signal of $D_2O$ was used as an internal standard. To determine the temperature gradients, a 0.01 molar solution of the complexes in question in $D_2O$ was produced. Of the respective solutions, spectra at various temperatures in the range between 46° C. and 26° C. were recorded. From these measurements, a temperature gradient of 0.145 ppm/K follows for the praseodymium complex (produced according to Example 6c).

Figure 2:
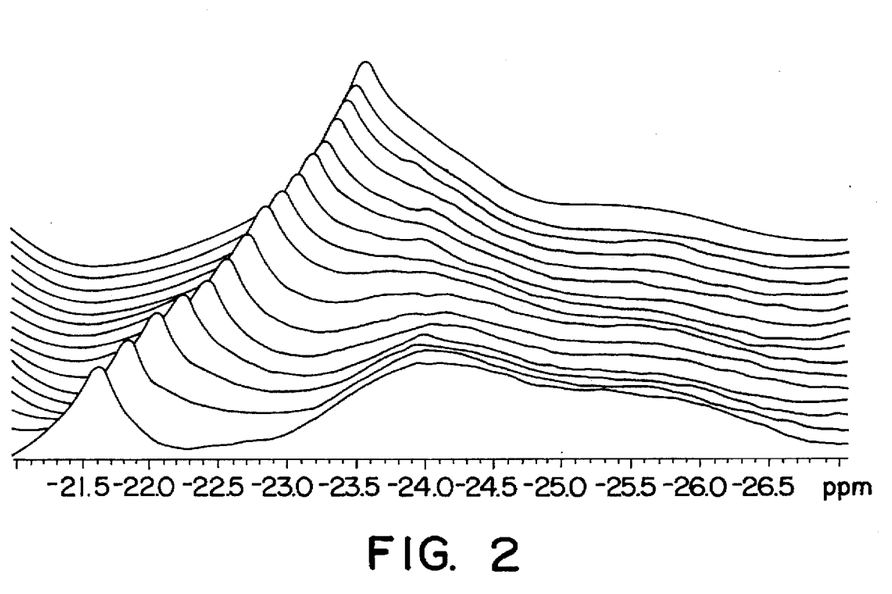
FIG. 2 shows the time change of the NMR spectrum during cooling of a praseodymium complex solution.

FIG. 2 shows the time change of the NMR spectrum during the cooling of the solution of the above-mentioned praseodymium complex. Taking into consideration the line width, a measuring accuracy of 0.3° C. results.

These data for five of the compounds shown in the Examples is shown in the following table.

| Substance Example No. | Central Atom | Signal-Transmitting Group | Temperature Gradient (ppm/K) | Line Width (Hz) | Chemical Shift (ppm) | Relative Accuracy of Measurement (ppm/Hz · K) |
| --- | --- | --- | --- | --- | --- | --- |
| 1d | Sm | $CH_2CH(OH)$-$CH_2OCH_3$ | 0.012 | 8 | −1.36 | $1.5 \times 10^{-3}$ |
| 2b | Sm | $CH_2CH(OH)$-$CH_2O^tBu$ | 0.011 | 8.5 | −3.50 | $1.3 \times 10^{-3}$ |
| 2c | Eu | $CH_2CH(OH)$-$CH_2O^tBu$ | 0.010 | 8 | −2.5 | $1.25 \times 10^{-3}$ |
| 6c | Pr | $CH_2CH_2OCH_3$ | 0.145 | 25 | −21 | $5.8 \times 10^{-3}$ |
| 6h | Eu | $CH_2CH_2OCH_3$ | −0.055 | 15 | 12 | $3.7 \times 10^{-3}$ |

A quite critical advantage of this family of compounds for localized in vivo $^1$H-NMR spectroscopy lies in the fact that the signals used for temperature measurement appear outside the spectral range of all endogenous substances, including tissue water. This allows the almost distortion-free measurement of temperature-sensitive signals thanks to greatly simplified suppression of intense background signals for NMR spectroscopy.

The great flexibility of the chemical structure of the ligand, which can be adapted to the measuring problem to be solved, offers another advantage. By appropriately adjusting, e.g., longitudinal relaxation time $T^1$ of the measurement signal, optimum sensitivity can be achieved. For localized spectroscopic methods, which are based on a spin echo, transversal relaxation time $T_2$ can be adjusted optimally in the same way.

The production of the complexing agents of general formula I (i.e., of compounds in which $R^1$ stands for a hydrogen atom) is done as described in European Patents EP 0 299 795, EP 0 434 345, EP 0 434 346 and EP 0 255 371.

Compounds of formula I, in which $R^3$ does not equate to hydrogen, can be produced as described in DE 41 40 779, by side chain —$R^2$—A being first introduced by reacting the corresponding epoxide with tricyclotridecane. After cleavage of the formyl group of the intermediate product produced, the product thus obtained is reacted with a compound of general formula III, in which X stands for a nucleofuge, e.g., for a halogen or a sulfonyloxy radical and $R^7$ stands for a hydrogen atom or for an acid protective group, preferably for a tert-butyl group.

Instead of the tricyclotridecane used above, tris (benzyloxycarbonyl) cyclene can also be alkylated with epoxides (see J. Chem. Soc. Perkin Trans. I, 12, 3329 [1991]).

The epoxides that are required for reactions can be produced according to the processes known to one skilled in the art.

The reaction of 1,4,7-triscarboxymethyl-1,4,7,10-tetraazacyclododecane with epoxides is done in solvents at temperatures of between 10° and 150° C., preferably at 50°–80° C. As solvents, all inert polar solvents are suitable. The reaction is done with the addition of bases. The bases can be added in solid or dissolved form. The bases that can be considered include lithium hydroxide, sodium hydroxide, potassium hydroxide, alkali- and alkaline-earth carbonates, and -oxides, or organic bases, such as tertiary amines, e.g., triethylamine or diisopropylethylamine, N-methylmorpholine or tetramethylpiperidine.

The reaction of 1,4,7-triscarboxymethyl-1,4,7,10-tetraazacyclododecane with halogen compounds can also be done in solid or liquid form. Preferred solvents are dioxane, tetrahydrofuran, dimethylformamide, dimethylacetamide and methanol, ethanol, propanol, isopropanol and water. The reaction is done with the addition of bases (as indicated above) at temperatures of between 40° C. and 150° C., preferably at 75° to 110° C.

The production of the metal complexes according to the invention from these complexing agents is done in the way that was disclosed in German laid-open specification DE 34 01 052, as well as in European Patent Applications EP 0 450 742 and EP 0 413 405, by dissolving or suspending the metal oxide or a metal salt (for example, nitrate, acetate, carbonate, chloride or sulfate) of the element of atomic numbers 21–29, 42, 44, 57–70 in water and/or a lower alcohol (such as methanol, ethanol or isopropanol) and reacting the equivalent amount of complexing ligand with the solution or suspension, and then, if desired, substituting present acid hydrogen atoms by cations of inorganic and/or organic bases or amino acids.

The neutralization of free acid groups that are optionally still present is done with the aid of inorganic bases (for example, hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methylglucamine and N,N-dimethylglucamine, as well as basic amino acids, such as, for example, lysine, arginine and ornithine or amides of initially neutral and acidic amino acids.

For the production of neutral complex compounds, for example, enough of the desired bases can be added to the acid complex salts in aqueous solution or suspension to ensure that the neutral point is reached. The solution obtained can then be evaporated to dryness in a vacuum. Often, it is advantageous to precipitate the neutral salts that are formed by adding water-miscible solvents, such as, for example, lower alcohols (methanol, ethanol, isopropanol and others), lower ketones (acetone and others), or polar ethers (tetrahydrofuran, dioxane, 1,2-dimethoxyethane and others) and thus to obtain crystallizates that are easily isolated and readily purified. It has proven especially advantageous to add the desired base as early as during complexing of the reaction mixture and as a result to eliminate a process step.

If the acid complex compounds contain several free acid groups, it is often advisable to produce neutral mixed salts that contain both inorganic and organic cations as counterions.

The pharmaceutical agents according to the invention are preferably produced in a concentration of 1 μmol-1 mol/l. They are generally dosed in amounts of 0.005–20 mmol/kg of body weight, preferably 0.05–5 mmol/kg of body weight.

They are intended for enteral and parenteral administration. The agents according to the invention meet the varied requirements for suitability as diagnostic tools for NMR spectroscopy. Further, they possess the high effectiveness that is necessary to burden the body with the smallest possible amounts of foreign substances and the good compatibility that is necessary to preserve the noninvasive nature of the studies.

The good water solubility and low osmolality of the agents according to the invention make it possible to produce highly concentrated solutions, so that the volume burden on the circulatory system is kept within reasonable limits and the dilution is compensated for by the bodily fluid. Further, the agents according to the invention exhibit not only high stability in vitro, but also surprisingly high stability in vivo so that any release or exchange of the ions that are bound in the complexes occurs only extremely slowly within the time that it takes for the new contrast media to be completely excreted again.

By using these very well-tolerated complexes as new measuring sensors, it has thus been possible to perform site-resolved spectroscopy in small volumes (e.g., 10 cm$^3$) and to determine temperature precisely in shorter measurement times without disruption or superposition by other molecules.

EXAMPLES

The following examples are used to explain the object of the invention, without intending that they be limited to this object.

EXAMPLE 1 a) 10-(2-Hydroxy-3-methoxy-propyl)-1,4,7-tris-carboxymethyl-1,4,7,10-tetraazacyclododecane 7.63 g (86.58 mmol) of glycidyl methyl ether and 10 g (28.86 mmol) of 1,4,7-triscarboxymethyl-1,4,7,10-tetraazacyclododecane are dissolved in a mixture of 50 ml of dioxane/80 ml of water, and the pH is brought to 10 with 6 N potassium hydroxide solution. It is stirred for 24 hours at 50° C. It is evaporated to dryness, the residue is taken up with 300 ml of water/50 ml of methanol and extracted twice with 100 ml of tert-butyl methyl ether. The aqueous solution is adjusted to pH 1 with 5 N hydrochloric acid and evaporated to dryness. The residue is boiled out (extracted) with 200 ml of methanol/80 ml of methylene chloride. It is cooled in an ice bath and precipitated potassium chloride is filtered out. The filtrate is concentrated by evaporation in a vacuum, the residue is dissolved in 45 ml of water/20 ml of ethanol and then put on a column of poly-(4-vinylpyridine). The product is eluted with a solution of ethanol/water 1:3. After concentration by evaporation in a vacuum, the residue is chromatographed on a reversed-phase column (RP 18/mobile solvent=gradient of water/tetrahydrofuran). After concentration by evaporation of the main fraction, 10.38 g (77% of theory) of a greatly hygroscopic, vitreous solid is obtained.

Water content: 7.0%

Analysis (relative to anhydrous substance):

Cld: C 49.76 H 7.89 N 12.89

Fnd: C 49.54 H 7.98 N 12.70 b) Lanthanum complex of 10-(2-hydroxy-3-methoxy-propyl)-1,4,7-tris-carboxymethyl-1,4,7,10-tetraazacyclododeca 5 g (11.51 mmol) of the title compound of Example 1a is dissolved in 50 ml of water and 1.87 g (5.75 mmol) of lanthanum oxide is added. It is stirred for 3 hours at 90° C. The solution is stirred for one hour with 2 ml of acidic ion exchanger (AMB 252c H$^+$) and 2 ml of weakly basic exchanger IRA 67 (OH$^-$ form) at room temperature. Exchanger is filtered out, and the filtrate is freeze-dried.

Yield: 6.56 g (95% of theory) of a vitreous solid

Water content: 4.9%

Analysis (relative to anhydrous substance):

Cld: C 37.90 H 5.48 N 9.82 La 24.35

Fnd: C 37.79 H 5.58 N 9.71 La 24.22 c) Praseodymium complex of 10-(2-hydroxy-3-methoxy-propyl)-1,4,7-tris-carboxymethyl-1,4,7,10-tetraazacyclododecane 5 g (11.51 mmol) of the title compound of Example 1a is dissolved in 50 ml of water and 3.66 g (11.51 mmol) of praseodymium(III) acetate is added. It is heated for 2 hours to 90° C. and then evaporated to dryness in a vacuum. The residue is taken up in 50 ml of water and again evaporated to dryness. The residue is dissolved in 100 ml of water and stirred for 1 hour with 2 ml of acidic ion exchanger (AMB 252c/H$^+$ form) and 5 ml of weakly basic exchanger (IRA 67/OH$^-$ form). Exchanger is filtered out, and the filtrate is freeze-dried.

Yield: 6.75 g (96% of theory) of a light green solid

Water content: 6.3%

Analysis (relative to anhydrous substance):

Cld: C 37.77 H 5.46 N 9.79 Pr 24.62

Fnd: C 37.56 H 5.69 N 9.61 Pr 24.48 d) Samarium complex of 10-(2-hydroxy-3-methoxy-propyl)-1,4,7-tris-carboxymethyl-1,4,7,10-tetraazacyclododecane Analogously to Example 1b, samarium oxide instead of lanthanum oxide was used.

Yield: 95% of theory of a colorless solid

Water content: 6.9%

Analysis (relative to anhydrous substance):

Cld: C 37.16 H 5.37 N 9.63 Sm 25.84

Fnd: C 36.95 H 5.45 N 9.49 Sm 25.67 e) Europium complex of 10-(2-hydroxy-3-methoxy-propyl)-1,4,7-tris-carboxymethyl-1,4,7,10-tetraazacyclododecane Analogously to Example 1b, europium oxide instead of lanthanum oxide was used.

Yield: 93% of theory of an amorphous powder

Water content: 9.4%

Analysis (relative to anhydrous substance):

Cld: C 37.06 H 5.36 N 9.60 Eu 26.05

Fnd: C 36.84 H 5.51 N 9.47 Eu 25.87 f) Holmium complex of 10-(2-hydroxy-3-methoxy-propyl)-1,4,7-tris-carboxymethyl-1,4,7,10-tetraazacyclododecane Analogously to Example 1b, holmium oxide instead of lanthanum oxide was used.

Yield: 97% of theory of a pale pink fluorescent solid

Water content: 7.2%

Analysis (relative to anhydrous substance):

Cld: C 36.25 H 5.24 N 9.39 Ho 27.65

Fnd: C 36.13 H 5.31 N 9.28 Ho 27.48 g) Dysprosium complex of 10-(2-hydroxy-3-methoxy-propyl)-1,4,7-tris-carboxymethyl-1,4,7,10-tetraazacyclododecane Analogously to Example 1b, dysprosium oxide instead of lanthanum oxide was used.

Yield: 95% of theory of a colorless amorphous powder
Water content: 8.1%
Analysis (relative to anhydrous substance):
Cld: C 36.40 H 5.26 N 9.43 Dy 27.36
Fnd: C 36.28 H 5.37 N 9.31 Dy 27.28

EXAMPLE 2 a) 10-(2-Hydroxy-3-tert-butyloxy-propyl)-1,4,7-tris-carboxymethyl-1,4,7,10-tetraazacyclododecane 11.27 g (86.58 mmol) of glycidyl-tert-butyl ether and 10 g (28.86 mmol) of 1,4,7-tris-carboxymethyl-1,4,7,10-tetraazacyclododecane are dissolved in a mixture of 50 ml of dioxane/80 ml of water, and the pH is brought to 10 with 6 N potassium hydroxide solution. It is stirred for 24 hours at 70° C. It is evaporated to dryness, the residue is taken up with 300 ml of water/50 ml of methanol and extracted twice with 100 ml of tert-butyl-methyl ether. The aqueous solution is adjusted to pH 1 with 5 N hydrochloric acid and evaporated to dryness. The residue is boiled out (extracted) with 200 ml of methanol/80 ml of methylene chloride. It is cooled in an ice bath and precipitated potassium chloride is filtered out. The filtrate is concentrated by evaporation in a vacuum, the residue is dissolved in 45 ml of water/20 ml of ethanol and then put on a column of poly-(4-vinylpyridine). The product is eluted with a solution of ethanol/water 1:3. After concentration by evaporation in a vacuum, the residue is chromatographed on a reversed-phase column (RP 18/mobile solvent=gradient of water/tetrahydrofuran). After concentration by evaporation of the main fraction, 10.38 g (71% of theory) of a strongly hygroscopic, vitreous solid is obtained.

Water content: 5.9%
Analysis (relative to anhydrous substance):
Cld: C 52.93 H 8.46 N 11.76
Fnd: C 52.80 H 8.51 N 11.58 b) Samarium complex of 10-(2-hydroxy-3-tert-butyloxy-propyl)-1,4,7-tris-carboxymethyl-1,4,7,10-tetraazacyclododecane 5 g (10.49 mmol) of the title compound of Example 2a is dissolved in 50 ml of water and 1.83 g (5.24 mmol) of samarium oxide is added. It is stirred for 3 hours at 90° C. The solution is stirred for one hour with 2 ml of acidic ion exchanger (AMB 252c/H$^+$ form) and 2 ml of weakly basic exchanger IRA 67/OH$^-$ form) at room temperature.

Yield: 6.77 g (96% of theory) of a vitreous solid
Water content: 7.2%
Analysis (relative to anhydrous substance):
Cld: C 40.43 H 5.98 N 8.98 Sm 24.10
Fnd: C 40.21 H 6.10 N 8.87 Sm 24.00 c) Praseodymium complex of 10-(2-hydroxy-3-tert-butyloxy-propyl)-1,4,7-tris-carboxymethyl-1,4,7,10-tetraazacyclododecane Analogously to Example 1c, the title compound of Example 2a instead of the title compound of Example 1a was used for complexing.

Yield: 93% of theory of a greenish amorphous powder
Water content: 5.9%
Analysis (relative to anhydrous substance):
Cld: C 41.05 H 6.07 N 9.12 Pr 22.93
Fnd: C 40.90 H 6.20 N 9.01 Pr 22.74 d) Dysprosium complex of 10-(2-hydroxy-3-tert-butyloxy-propyl)-1,4,7-tris-carboxymethyl-1,4,7,10-tetraazacyclododecane Analogously to Example 2b, dysprosium oxide instead of samarium oxide was used.

Yield: 95% of theory of a colorless amorphous powder
Water content: 7.4%
Analysis (relative to anhydrous substance):
Cld: 39.66 H 5.86 N 8.81 Dy 25.55
Fnd: 39.49 H 5.98 N 8.70 Dy 25.38 e) Europium complex of 10-(2-hydroxy-3-tert-butyloxy-propyl)-1,4,7-tris-carboxymethyl-1,4,7,10-tetraazacyclododecane Analogously to Example 2b, europium oxide instead of samarium oxide was used.

Yield: 97% of theory of a colorless solid
Water content: 8.7%
Analysis (relative to anhydrous substance):
Cld: C 40.32 H 5.92 N 8.96 Eu 24.29
Fnd: C 49.18 H 5.99 N 8.71 Eu 24.05 f) Lanthanum complex of 10-(2-hydroxy-3-tert-butyloxy-propyl)-1,4,7-tris-carboxymethyl-1,4,7,10-tetraazacyclododecane Analogously to Example 2b, lanthanum oxide instead of samarium oxide was used.

Yield: 94% of theory of a colorless amorphous powder
Water content: 8.1%
Analysis (relative to anhydrous substance):
Cld: C 41.18 H 6.09 N 9.15 La 22.68
Fnd: C 41.04 H 6.17 N 9.02 La 22.49 g) Holmium complex of 10-(2-hydroxy-3-tert-butyloxy-propyl)-1,4,7-tris-carboxymethyl-1,4,7,10-tetraazacyclododecane Analogously to Example 2b, holmium oxide instead of samarium oxide was used.

Yield: 97% of theory of a light red fluorescent powder
Water content: 5.9%
Analysis (relative to anhydrous substance):
Cld: C 39.51 H 5.84 N 8.78 Ho 25.83
Fnd: C 39.37 H 5.98 N 8.60 Ho 25.67

EXAMPLE 3 a) Lanthanum complex of 10-(2-hydroxy-propyl)-1,4,7-tris-(carboxymethyl)-1,4,7,10-tetraazacyclododecane 5 g (12.36 mmol) of 10-(2-hydroxy-propyl)-1,4,7-tris-(carboxymethyl)-1,4,7,10-tetraazacyclododecane is dissolved in 50 ml of water and 2.01 g (6.18 mmol) of lanthanum oxide is added. It is stirred for 3 hours at 90° C. The solution is stirred for one hour with 2 ml of acidic ion exchanger (AMB 252c/H$^+$ form) and 2 ml of weakly basic exchanger (IRA 67/OH$^-$ form) at room temperature. Exchanger is filtered out, and the filtrate is freeze-dried.

Yield: 6.53 g (94% of theory) of a vitreous solid
Water content: 3.8%
Analysis (relative to anhydrous substance):
Cld: C 37.79 H 5.41 N 10.37 La 25.71
Fnd: C 37.58 H 5.60 N 10.18 La 25.52 b) Samarium complex of 10-(2-hydroxy-propyl)-1,4,7-tris-(carboxymethyl)-1,4,7,10-tetraazacyclododecane Analogously to Example 3a, title compound 3b was produced from samarium oxide and 10-(2-hydroxy-propyl)-1,4,7-tris-(carboxymethyl)-1,4,7,10-tetraazacyclododecane.

Yield: 95% of theory of a colorless solid
Water content: 6.1%

Analysis (relative to anhydrous substance):

Cld: C 37.00 H 5.30 N 10.15 Sm 27.25

Fnd: C 36.88 H 5.41 N 10.02 Sm 27.10 c) Holmium complex of 10-(2-hydroxy-propyl)-1,4,7-tris-(carboxymethyl)-1,4,7,10-tetraazacyclododecane Analogously to Example 3a, title compound 7c was produced from holmium oxide and 10-(2-hydroxy-propyl)-1,4,7-tris-(carboxymethyl)-1,4,7,10-tetraazacyclododecane.

Yield: 97% of theory of a pale rose-colored solid

Water content: 8.7%

Analysis (relative to anhydrous substance):

Cld: C 36.05 H 5.16 N 9.89 Ho 29.12

Fnd: C 35.87 H 5.29 N 9.71 Ho 29.01 d) Europium complex of 10-(2-hydroxy-propyl)-1,4,7-tris-(carboxymethyl)-1,4,7,10-tetraazacyclododecane Analogously to Example 3a, title compound 3d was produced from europium oxide and 10-(2-hydroxy-propyl)-1,4,7-tris-(carboxymethyl)-1,4,7,10-tetraazacyclododecane.

Yield: 97% of theory of colorless solid

Water content: 5.7%

Analysis (relative to anhydrous substance):

Cld: C 36.90 H 5.28 N 10.12 Eu 27.46

Fnd: C 36.71 H 5.41 N 9.97 Eu 27.31 e) Praseodymium complex of 10-(2-hydroxy-propyl)-1,4,7-tris-(carboxymethyl)-1,4,7,10-tetraazacyclododecane Analogously to Example 1c, 10-(2-hydroxy-propyl)-1,4,7-tris-(carboxymethyl)-1,4,7,10-tetraazacyclododecane instead of the title compound of Example 1a was used for complexing.

Yield: 98% of theory of greenish solid

Water content: 5.9%

Analysis (relative to anhydrous substance):

Cld: C 37.65 H 5.39 N 10.33 Pr 25.98

Fnd: C 37.48 H 5.48 N 10.18 Pr 25.81

EXAMPLE 4 a) 10-(6-Hydroxy-2,2-dimethyl-1,3-dioxepan-5-yl)-1,4,7-tris(benzyloxycarbonyl)-1,4,7,10-tetraazacyclododecane 40 g (126.4 mmol) of 10-(6-hydroxy-2,2-dimethyl-1,3-dioxepan-5-yl)-1,4,7,10-tetraazacyclododecane is dissolved in 400 ml of methylene chloride and 42.21 g (417.1 mmol) of triethylamine is added. At 0° C., 71.16 g (417.1 mmol) of benzyl chloroformate is instilled within one hour and stirred for one hour at 0° C., then overnight at room temperature. It is mixed with 500 ml of water and stirred for 30 minutes. The organic phase is separated, dried on magnesium sulfate and concentrated by evaporation in a vacuum. The residue is chromatographed on silica gel (mobile solvent =methylene chloride/acetone 20:1).

Yield: 79.05 g (87% of theory) of a colorless oil

Analysis:

Cld: C 65.16 H 7.01 N 7.79

Fnd: C 65.08 H 7.15 N 7.66 b) 10-(1-(2,2-Dimethyl-1,3-dioxolan-4-yl)-2-hydroxy-ethyl)-1,4,7-tris(benzyloxy-carbonyl)-1,4,7,10-tetraazacyclododecane 7.8 g (108.5 mmol) of the title compound of Example 4a and 19.61 g (113.9 mmol) of p-toluenesulfonic acid are dissolved in 800 ml of ethanol and stirred for 3 hours at 70° C. It is evaporated to dryness, the residue is taken up with 500 ml of toluene and again evaporated to dryness. This residue is taken up with 600 ml of toluene and 53.4 ml (434 mmol) of 2,2-dimethoxypropane is added. Then, it is stirred for 2 hours at 80° C. The solution is cooled to room temperature and shaken out 3 times with 400 ml of 3 N sodium hydroxide solution. The organic phase is dried on magnesium sulfate and evaporated to dryness in a vacuum. The residue is chromatographed on silica gel (Mobile solvent =methylene chloride/acetone 15:1).

Yield: 56.94 g (73% of theory) of a colorless oil

Analysis:

Cld: C 65.16 H 7.01 N 7.79

Fnd: C 64.95 H 6.88 N 7.68 c) 10-[1-(2,2-Dimethyl-1,3-dioxolan-4-yl)-2-methoxy-ethyl]-1,4,7-tris(benzyloxycarbonyl)-1,4,7,10-tetraazacyclododecane 21.46 g (382.5 mmol) of potassium hydroxide (finely powdered) as well as 500 mg of tetrabutylammonium hydrogen sulfate are added to 55 g (76.5 mmol) of the title compound of Example 4b in 400 ml of methylene chloride. Within one hour, 12.61 g (100 mmol) of dimethyl sulfate is instilled with vigorous stirring at room temperature. It is stirred for 12 hours at room temperature. 400 ml of ice water is added and stirred for 15 minutes. The organic phase is separated, dried on magnesium sulfate and concentrated by evaporation in a vacuum. The residue is chromatographed on silica gel (mobile solvent =methylene chloride/acetone 20:1).

Yield: 52.14 g (93% of theory) of a colorless oil

Analysis:

Cld: C 65.56 H 7.15 N 7.64

Fnd: C 65.38 H 7.24 N 7.55 d) 1-[1-(2,2-Dimethyl-1,3-dioxolan-4-yl)-2-methoxyethyl]-1,4,7,10-tetraazacyclododecane 51 g (69.6 mmol) of the title compound of Example 4c is dissolved in 600 ml of ethanol and 5 g of palladium catalyst (10% Pd/C) is added. It is hydrogenated overnight at room temperature. The catalyst is filtered out, and the filtrate is evaporated to dryness in a vacuum.

Yield: 23 g (quantitative) of vitreous solid

Analysis:

Cld: C 58.15 H 10.37 N 16.95

Fnd: C 58.02 H 10.45 N 16.87 e) 10-(1-Methoxymethyl-2,3-dihydroxypropyl)-1,4,7-tris (carboxymethyl)-1,4,7,10-tetraazacyclododecane 8.35 g (25.28 mmol) of the title compound of Example 4d is dissolved in 50 ml of water and 14.05 g (101.12 mmol) of bromoacetic acid is added. The pH is brought to 9.5 with 6 N potassium hydroxide solution. It is heated to 60° C. and the pH is kept between 9.5–10 by adding 6 N potassium hydroxide solution. After 24 hours of stirring at 60° C., it is cooled in an ice bath, adjusted to pH 1 with concentrated hydrochloric acid and evaporated to dryness in a vacuum. The residue is dissolved in a little water and put on a cation-exchange column (IR 120). After flushing with water, the ligand is eluted with 0.5 N ammonia-water solution. The fractions are concentrated by evaporation, the ammonium salt is taken up with a little water and put on an anion-exchange column (IRA 67). It is washed first with water and then eluted with 0.5 N aqueous formic acid. It is concentrated by evaporation in a vacuum, the residue is dissolved in a little hot methanol and acetone is added. After cooling in an ice bath, the title compound crystallizes out.

Yield: 6.94 g (53% of theory) of an amorphous, hygroscopic powder

Water content: 10.3%

Analysis (relative to anhydrous substance):

Cld: C 49.13 H 7.81 N 12.06

Fnd: C 49.02 H 7.95 N 11.87 f) Lanthanum complex of 10-(1-methoxymethyl-2,3-dihydroxypropyl)-1,4,7-tris(carboxymethyl)-1,4,7,10-tetraazacyclododecane 5 g (10.76 mmol) of the title compound of Example 4e is dissolved in 50 ml of water and 1.75 g (5.38 mmol) of lanthanum oxide is added. It is stirred for 3 hours at 90° C. The solution is stirred for one hour with 2 ml of acidic ion exchanger (AMB 252c/H$^+$ form) and 2 ml of weakly basic exchanger (IRA 67/OH$^-$ form) at room temperature. Exchanger is filtered out, and the filtrate is freeze-dried.

Yield: 6.76 g (97% of theory) of a vitreous solid

Water content: 6.1%

Analysis (relative to anhydrous substance):

Cld: 38.01 H 5.54 N 9.33 La 23.14

Fnd: 37.83 H 5.67 N 9.18 La 23.02 g) Dysprosium complex 10-(1-methoxymethyl-2,3-dihydroxypropyl)-1,4,7-tris(carboxymethyl)-1,4,7,10-tetraazacyclododecane Analogously to Example 4f, dysprosium oxide instead of lanthanum oxide was used.

Yield: 93% of theory of a vitreous solid

Water content: 8.1%

Analysis (relative to anhydrous substance):

Cld: C 36.57 H 5.33 N 8.98 Dy 26.04

Fnd: C 36.41 H 5.41 N 8.77 Dy 25.84 h) Praseodymium complex of 10-(1-methoxymethyl-2,3-dihydroxypropyl)-1,4,7-tris(carboxymethyl)-1,4,7,10-tetraazacyclododecane Analogously to Example 1c, the title compound of Example 4e instead of the title compound of Example 1a was used for complexing.

Yield: 95% of theory of a greenish-colored solid

Water content: 8.3%

Analysis (relative to anhydrous substance):

Cld: C 37.88 H 5.52 N 9.30 Pr 23.39

Fnd: C 37.69 H 5.63 N 9.13 Pr 23.20 i) Europium complex of 10-(1-methoxymethyl-2,3-dihydroxypropyl-1,4,7-tris(carboxymethyl)-1,4,7,10-tetraazacyclododecane Analogously to Example 4f, europium oxide instead of lanthanum oxide was used.

Yield: 98% of theory of a colorless amorphous powder

Water content: 7.4%

Analysis (relative to anhydrous substance):

Cld: C 37.20 H 5.42 N 9.13 Eu 24.77

Fnd: C 37.01 H 5.61 N 9.04 Eu 24.58

EXAMPLE 5 a) 1,3-Dimethoxy-propyl-2-trifluoromethanesulfonate 46.96 g (166 mmol) of trifluoromethanesulfonic anhydride is instilled in 20 g (166 mmol) of 1,3-dimethoxy-2-hydroxypropane and 16.8 g (166 mmol) of triethylamine in 400 ml of diethyl ether at −20° C. and stirred for 2 hours at this temperature. Then, it is stirred for 2 hours at 0° C. It is poured in 300 ml of 20% aqueous common salt solution and stirred vigorously. The organic phase is separated and extracted twice with 200 ml of 20% aqueous common salt solution. The organic phase is dried on magnesium sulfate and concentrated by evaporation in a vacuum.

Yield: 39.77 g (95% of theory) of a colorless oil (~ 97% content according to gradient chromatography) (It is further reacted without purification in Example 5b)

Analysis:

Cld: C 28.57 H 4.40 F 26.60 S 12.69

Fnd: C 28.81 H 4.65 F 26.30 S 12.38 b) 10-[1,1-Di(methoxymethyl)-methyl]-1,4,7-tris-(benzyloxycarbonyl)-1,4,7,10-tetraazacyclododecane 39 g (154.6 mmol) of the title compound of Example 5a and 44.43 g (77.3 mmol) of 1,4,7-tris-(benzyloxycarbonyl)-1,4,7,10-tetraazacyclododecane (produced according to Chem. Soc., Perkin Trans. 1, 12:3329, 1991) and 85.14 g (616 mmol) of potassium carbonate in 800 ml acetonitrile are refluxed for 24 hours. Solid is filtered out, and the filtrate is evaporated to dryness in a vacuum. The residue is taken up in 700 ml of methylene chloride and extracted twice with 300 ml of water. The organic phase is dried on magnesium sulfate and concentrated by evaporation in a vacuum. The residue is chromatographed on silica gel (mobile solvent =methylene chloride/methanol 20:1).

Yield: 18.31 g (35% of theory relative to amine) of a colorless oil

Analysis:

Cld: C 65.66 H 7.15 N 8.28

Fnd: C 65.47 H 7.28 N 8.13 c) 1-[1,1-Di(methoxymethyl)-methyl]-1,4,7,10-tetraazacyclododecane 18 g (26.6 mmol) of the title compound of Example 5b is dissolved in 300 ml of ethanol and 4 g of palladium catalyst (10% Pd/C) is added. It is hydrogenated for 12 hours at room temperature. The catalyst is filtered out, and the filtrate is evaporated to dryness in a vacuum.

Yield: 7.3 g (quantitative) of a yellowish, viscous oil

Analysis:

Cld: C 56.90 H 11.02 N 20.42

Fnd: C 56.71 H 11.10 N 20.28 d) 10-[1-Di(methoxymethyl)-methyl]-1,4,7-tris(carboxymethyl)-1,4,7,10-tetraazacyclododecane 6.94 g (25.28 mmol) of the title compound of Example 5c is dissolved in 50 ml of water and 14.05 g (101.12 mmol) of bromoacetic acid is added. The pH is brought to 9.5 with 6 N potassium hydroxide solution. It is heated to 60° C. and the pH is kept between 9.5–10 by adding 6 N potassium hydroxide solution. After 24 hours of stirring at 60° C., it is cooled in an ice bath, adjusted to pH 1 with concentrated hydrochloric acid and evaporated to dryness in a vacuum. The residue is dissolved in a little water and put on a cation-exchange column (IR 120). After flushing with water, the ligand is eluted with 0.5 N ammonia-water solution. The fractions are concentrated by evaporation, the ammonium salt is taken up with a little water and put on an anion-exchange column (IRA 67). It is washed first with water and then eluted with 0.5 N aqueous formic acid. It is concentrated by evaporation in a vacuum, the residue is dissolved in a little hot ethanol and acetone is added. After cooling in an ice bath, the title compound crystallizes out.

Yield: 7.71 g (61% of theory) of a hygroscopic solid

Water content: 10.3%

Analysis (relative to anhydrous substance):

Cld: C 50.88 H 8.09 N 12.49

Fnd: C 50.64 H 8.20 N 12.27 e) Lanthanum complex of 10-[1-di(methoxymethyl)-methyl]-1,4,7-tris(carboxymethyl)-1,4,7,10-tetraazacyclododecane 5 g (11.15 mmol) of the title compound of Example 5d is dissolved in 50 ml of water and 1.82 g (5.57 mmol) of lanthanum oxide is added. It is stirred for 3 hours at 90° C.

The solution is stirred for one hour with 2 ml of acidic ion exchanger (AMB 252c/H⁺ form) and 2 ml of weakly basic exchanger (IRA 67/OH⁻ form) at room temperature. Exchanger is filtered out, and the filtrate is freeze-dried.

Yield: 6.73 g (96% of theory) of a vitreous solid

Water content: 6.7%

Analysis (relative to anhydrous substance):

Cld: C 39.05 H 5.69 N 9.59 La 23.77

Fnd: C 38.84 H 5.78 N 9.41 La 23.60 f) Dysprosium complex of 10-[1-di(methoxymethyl)-methyl]-1,4,7-tris(carboxymethyl)-1,4,7,10-tetraazacyclododecane Analogously to Example 5e, dysprosium oxide instead of lanthanum oxide was used.

Yield: 93% of theory of a colorless solid

Water content: 7.3%

Analysis (relative to anhydrous substance):

Cld: C 37.54 H 5.47 N 9.21 Dy 26.73

Fnd: C 37.71 H 5.55 N 9.05 Dy 26.54 g) Europium complex of 10-[1-di(methoxymethyl)-methyl]-1,4,7-tris(carboxymethyl)-1,4,7,10-tetraazacyclododecane Analogously to Example 5e, europium oxide instead of lanthanum oxide was used.

Yield: 95% of theory of a colorless amorphous powder

Water content: 8.5%

Analysis (relative to anhydrous substance):

Cld: C 38.20 H 5.57 N 9.38 Eu 25.43

Fnd: C 38.03 H 5.68 N 9.24 Eu 25.28 h) Praseodymium complex of 10-[1-di(methoxymethyl)-methyl]-1,4,7-tris(carboxymethyl)-1,4,7,10-tetraazacyclododecane Analogously to Example 1c, the title compound of Example 5d instead of title compound 1a was used for complexing.

Yield: 96% of theory of a green solid

Water content: 3.9%

Analysis (relative to anhydrous substance):

Cld: C 38.92 H 5.67 N 9.55 Pr 24.03

Fnd: C 38.73 H 5.75 N 9.47 Pr 23.84

EXAMPLE 6 a) 10-(3-Oxa-butyl)-1,4,7-tris-(carboxymethyl)-1,4,7,10-tetraazacyclododecane 3 g (8.66 mmol) of 1,4,7-tris-(carboxymethyl)-1,4,7,10-tetraazacyclododecane is stirred in 50 ml of dimethylformamide for 10 hours with 1.57 g (11.29 mmol) of 2-methoxyethyl bromide and 4.15 g of potassium carbonate at 90° C. It is concentrated by evaporation in a vacuum and the residue is spread between 100 ml of water and 50 ml of diethyl ether. The aqueous phase is adjusted to pH 2 with 5 N hydrochloric acid and evaporated to dryness. The residue is refluxed with 200 ml of methanol, the undissolved material is filtered out, it is evaporated to dryness in a vacuum, the residue is dissolved in 50 ml of water, adjusted to pH 2 with 5 N hydrochloric acid and the solution is put on a column with 200 ml of cation exchanger IRC 50. It is eluted first with 0.5 l of water, which is discarded. Then, it is eluted with 0.5 l of 0.5 N ammonia solution. It is evaporated almost to dryness in a vacuum, mixed with 100 ml of water and enough cation exchanger IRC 50 is added with stirring until pH 3.5 is reached. The solution is then filtered and freeze-dried. 2.49 g of the title compound with a water content of 4.30% is obtained.

Analysis (relative to anhydrous substance):

Cld: C 50.48 H 7.79 N 13.85

Fnd: C 50.31 H 7.91 N 13.95 b) Dysprosium complex of 10-(3-oxabutyl)-1,4,7-tris-(carboxymethyl)-1,4,7,10-tetraazacyclododecane 2 g (4.95 mmol) of anhydrous substance of the title compound of Example 6a is stirred in 25 ml of water with 922 mg of dysprosium oxide for 8 hours at 85° C. It is cooled to room temperature and the solution is stirred for 1 hour with 1 ml of acidic ion exchanger (AMB 252c, H⁺ form) and 1 ml of basic ion exchanger (IRA 67, OH⁻ form). It is filtered, freeze-dried and 2.54 g of the title compound is obtained.

Water content: 5.1%

Analysis (relative to anhydrous substance):

Cld: C 36.20 H 5.18 Dy 28.81 N 9.93

Fnd: C 36.77 H 5.32 Dy 28.66 N 10.05 c) Praseodymium complex of 10-(3-oxabutyl)-1,4,7-tris-(carboxymethyl)-1,4,7,10-tetraazacyclododecane 2.5 g (6.18 mmol, anhydrous substance) of the title compound of Example 6a is stirred in 30 ml of water with 1.019 g (3.09 mmol) of praseodymium oxide for 5 hours at 85° C. It is cooled to room temperature and the solution is stirred for 1 hour with 1.3 ml of acidic ion exchanger (AMB 252c, H⁺ form) and 1.3 ml of basic ion exchanger (IRA 67, OH⁻ form). It is filtered, freeze-dried and 3.10 g of the title compound is obtained with a water content of 4.05% as light green solid.

Analysis (relative to anhydrous substance):

Cld: C 37.64 H 5.39 N 10.33 Pr 25.98

Fnd: C 37.96 H 5.49 N 10.32 Pr 25.69 d) Holmium complex of 10-(3-oxabutyl)-1,4,7-tris-(carboxymethyl)-1,4,7,10-tetraazacyclododecane Analogously to Example 6c, holmium(III) oxide instead of praseodymium oxide is used.

Yield: 90% of theory of a colorless solid

Water content: 4.90%

Analysis (relative to anhydrous substance):

Cld: C 36.05 H 5.16 Ho 29.12 N 9.89

Fnd: C 36.35 H 5.41 Ho 29.01 N 9.97 e) Ytterbium complex of 10-(3-oxabutyl)-1,4,7-tris-(carboxymethyl)-1,4,7,10-tetraazacyclododecane Analogously to Example 6c, ytterbium(III) oxide instead of praseodymium oxide is used.

Yield: 90% of theory of a colorless solid

Water content: 5.3%

Analysis (relative to anhydrous substance):

Cld: C 35.54 H 5.09 N 9.75 Yb 30.12

Fnd: C 35.80 H 5.31 N 9.80 Yb 30.07 f) Samarium complex of 10-(3-oxabutyl)-1,4,7-tris-(carboxymethyl)-1,4,7,10-tetraazacyclododecane Analogously to Example 6c, samarium(III) oxide instead of praseodymium oxide is used.

Yield: 93% of theory of a colorless solid

Water content: 5.00%

Analysis (relative to anhydrous substance):

Cld: C 37.00 H 5.30 N 10.15 Sm 27.24

Fnd: C 37.32 H 5.52 N 10.09 Sm 27.02 g) Gadolinium complex of 10-(3-oxabutyl)-1,4,7-tris-(carboxymethyl)-1,4,7,10-tetraazacyclododecane Analogously to Example 6c, gadolinium oxide instead of praseodymium oxide is used.

Yield: 91% of theory of a colorless solid

Water content: 5.05%

Analysis (relative to anhydrous substance):

Cld: C 36.54 H 5.23 Gd 28.14 N 10.02

Fnd: C 37.02 H 5.27 Gd 27.88 N 10.17 h) Europium complex of 10-(3-oxabutyl)-1,4,7-tris-(carboxymethyl)-1,4,7,10-tetraazacyclododecane Analogously to Example 6c, europium(III) oxide instead of praseodymium oxide is used.

Yield: 95% of theory of a colorless solid

Water content: 4.30%

Analysis (relative to anhydrous substance):

Cld: C 36.89 H 5.28 Eu 27.46 N 10.12

Fnd: C 37.31 H 5.40 Eu 27.00 N 10.22

EXAMPLE 7 a) 10-(4,4-Dimethyl-3-oxa-pentyl)-1,4,7-tris-(carboxymethyl)-1,4,7,10-tetraazacyclododecane 5 g (14.43 mmol) of 1,4,7-tris-(carboxymethyl)-1,4,7,10-tetraazacyclododecane is stirred in 75 ml of dimethylformamide for 18 hours with 3.14 g (17.35 mmol) of (2-bromoethyl)-tert-butyl ether and 6.50 g of potassium carbonate at 95° C. It is concentrated by evaporation in a vacuum and the residue is dissolved in 100 ml of water, the pH is adjusted to 2 by adding 12 N hydrochloric acid and the solution is put on a column of 320 ml of cation exchanger IR-120 ($H^+$ form). It is eluted with 2 l of water, which is discarded, then with 2 l of 0.5 N ammonia solution. This solution is concentrated by evaporation in a vacuum, the residue is dissolved in 100 ml of water. With stirring, enough cation exchanger IR-120 is added in portions up to pH 3.5. The solution is filtered and freeze-dried and 4.19 g of the title compound is obtained as white solid with a water content of 6.3%.

Analysis (relative to anhydrous substance):

Cld: C 53.79 H 8.58 N 12.54

Fnd: C 54.01 H 8.49 N 12.70 b) Dysprosium complex of 10-(4,4-dimethyl-3-oxapentyl)-1,4,7-tris(carboxymethyl)-1,4,7,10-tetraazacyclododecane 2.5 g (5.60 mmol, anhydrous substance) of the title compound of Example 7a is stirred with 1.044 g of dysprosium oxide (2.80 mmol) in 30 ml of water for 5 hours at 90° C. After cooling, the solution is stirred for 1 hour with 1.2 ml of acidic ion exchanger (AMB 252 c, $H^+$ form) and 1.2 ml of basic ion exchanger (IRA 67, $OH^-$ form). It is filtered, freeze-dried and 2.55 g of the title compound is obtained as solid.

Water content: 4.35%

Analysis (relative to anhydrous substance):

Cld: C 39.63 H 5.82 Dy 26.81 N 9.24

Fnd: C 39.83 H 5.90 Dy 26.60 N 9.32 c) Praseodymium complex of 10-(4,4-dimethyl-3-oxapentyl)-1,4,7-tris(carboxymethyl)-1,4,7,10-tetraazacyclododecane Analogously to Example 7b, praseodymium(III) oxide instead of dysprosium oxide is used.

Yield: 72% of a light green solid

Water content: 4.2%

Analysis (relative to anhydrous substance):

Cld: C 41.10 H 6.04 N 9.59 Pr 24.11

Fnd: C 41.29 H 6.30 N 9.68 Pr 23.95

EXAMPLE 8 a) 1,4-Di[4,7,10-tris(benzyloxycarbonyl)-1,4,7,10-tetraazacyclododecan-1-yl]-2,3-dihydroxybutane 44.43 g (77.3 mmol) of 1,4,7-tris-(benzyloxycarbonyl)-1,4,7,10-tetraazacyclododecane (produced according to Chem. Soc. Perkin Trans 1, 12: 3329, 1991) and 2.21 g (25.67 mmol) of 1, 2-3,4-diepoxybutane in 200 ml of n-butanol are refluxed for 3 days. It is evaporated to dryness in a vacuum and the residue is chromatographed on silica gel (mobile solvent: methylene chloride/hexane/acetone =20/10/1).

Yield: 15.22 g (48% of theory relative to 1,2-3,4-diepoxybutane) of a viscous oil Analysis:

Cld: C 66.11 H 6.69 N 9.07

Fnd: C 66.03 H 6.80 N 9.15 b) 1,4-Di[4,7,10-tris(benzyloxycarbonyl)-1,4,7,10-tetraazacyclododecan-1-yl]-2,3-dimethoxybutane 8.52 g (60 mmol) of methyl iodide is added to 15 g (12.14 mmol) of the title compound of Example 8a and 1.44 g (60 mmol) of sodium hydride in 200 ml of dimethylformamide and stirred for 48 hours at 60° C. 1000 ml of water is added and extracted twice with 300 ml of ethyl acetate. The combined organic phases are extracted twice with 500 ml of water, then the organic phase is dried on magnesium sulfate and evaporated to dryness in a vacuum. The residue is purified on silica gel (mobile solvent: methylene chloride/hexane/acetone =20/10/1).

Yield: 13.65 g (89% of theory) of a colorless oil

Analysis:

Cld: C 66.54 H 6.86 N 8.87

Fnd: C 66.39 H 6.95 N 8.71 c) 1,4-Di[1,4,7,10-tetraazacyclododecan-1-yl]-2,3-dimethoxybutane 13.5 g (10.68 mmol) of the title compound of Example 8b is dissolved in 300 ml of ethanol and 4 g of palladium catalyst (10% Pd/C) is added. It is hydrogenated for 12 hours at room temperature. The catalyst is filtered out, and the filtrate is evaporated to dryness in a vacuum.

Yield: 4.9 g (quantitative) of a slightly cream-colored solid

Analysis:

Cld: C 57.61 H 10.99 N 24.43

Fnd: C 57.51 H 10.93 N 24.48 d) 1,4-Di[4,7,10-tris(carboxymethyl)-1,4,7,10-tetraazacyclododecan-1-yl]-2,3-dimethoxybutane 4.8 g (10.46 mmol) of the title compound of Example 8c is dissolved in 80 ml of water and 13.96 g (100.5 mmol) of bromoacetic acid is added. The pH is brought to 9.5 with 6 N potassium hydroxide solution. It is heated to 60° C. and a pH between 9.5–10 is obtained by adding 6 N potassium hydroxide solution. After 24 hours of stirring at 60° C., it is cooled in an ice bath, adjusted to pH 1 with concentrated hydrochloric acid and evaporated to dryness in a vacuum. The residue is dissolved in a little water and put on a cation-exchange column (IR 120). After flushing with water, the ligand is eluted with 0.5 N ammonia-water solution. The fractions are concentrated by evaporation, the ammonium salt is taken up with a little water and put on an anion-exchange column (IRA 67). It is washed first with water and then eluted with 0.5 N aqueous formic acid. It is concentrated by evaporation in a vacuum, the residue is dissolved in a little hot ethanol and acetone is added. After cooling in an ice bath, the title compound crystallizes out.

Yield: 4.77 g (51% of theory) of a hygroscopic solid

Water content: 9.7%

Analysis (relative to anhydrous substance):

Cld: C 50.61 H 7.74 N 13.89

Fnd: C 50.50 H 7.81 N 13.78 e) Bis-praseodymium complex of 1,4-di[4,7,10-tris(carboxymethyl)-1,4,7,10-tetraazacyclododecan-1-yl]-2,3-dimethoxybutane 4.5 g (5.577 mmol) of the title compound of Example 8d is dissolved in 50 ml of water and 1.84 g (5.577 mmol) of praseodymium oxide is added. It is stirred for 3 hours at 90° C. The solution is stirred for one hour with 2 ml of acidic ion exchanger (AMB 252c/H$^+$ form) and 2 ml of weakly basic exchanger (IRA 67/OH$^-$ form) at room temperature. Exchanger is filtered out, and the filtrate is freeze-dried.

Yield: 6.47 g (97% of theory) of a vitreous solid

Water content: 6.3%

Analysis (relative to anhydrous substance):

Cld: C 37.72 H 5.21 N 10.35 Pr 26.03

Fnd: C 37.65 H 5.29 N 10.24 Pr 25.95

EXAMPLE 9 a) 1,7-Di[4,7,10-tris(benzyloxycarbonyl)-1,4,7,10-tetraazacyclododecan-1-yl]-2,6-dihydroxy-4-oxaheptane 44.43 g (77.3 mmol) of 1,4,7-tris-(benzyloxycarbonyl)-1,4,7,10-tetraazacyclododecane (produced according to Chem. Soc. Perkin Trans 1, 12: 3329, 1991) and 3.34 g (25.67 mmol) of 1, 2-6,7-diepoxy-4-oxa-heptane in 200 ml of n-butanol are refluxed for 3 days. It is evaporated to dryness in a vacuum and the residue is chromatographed on silica gel (mobile solvent: methylene chloride/hexane/acetone =20/10/1).

Yield: 17.74 g (54% of theory relative to 1,2-6, 7-diepoxy-4-oxa-heptane) of a viscous oil.

Analysis:

Cld: C 65.71 H 6.77 N 8.76

Fnd: C 65.65 H 6.84 N 8.70 b) 1,7-Di[4,7,10-tris(benzyloxycarbonyl)-1,4,7,10-tetraazacyclododecan-1-yl]-2,6-dimethoxy-4-oxaheptane 9.65 g (68 mmol) of methyl iodide is added to 17.5 g (13.68 mmol) of the title compound of Example 9a and 1.64 g (68 mmol) of sodium hydride in 230 ml of dimethylformamide and it is stirred for 48 hours at 60° C. 1000 ml of water is added and extracted twice with 300 ml of ethyl acetate. The combined organic phases are extracted twice with 500 ml of water, then the organic phase is dried on magnesium sulfate and evaporated to dryness in a vacuum. The residue is purified on silica gel (mobile solvent: methylene chloride/hexane/acetone =20/10/1).

Yield: 15.74 g (88% of theory) of a colorless oil

Analysis:

Cld: C 66.14 H 6.94 N 8.57

Fnd: C 64.07 H 6.91 N 8.61 c) 1,7-Di(1,4,7,10-tetraazacyclododecan-1-yl)-2,6-dimethoxy-4-oxaheptane 15.5 g (11.85 mmol) of the title compound of Example 9b is dissolved in 300 ml of ethanol and 4 g of palladium catalyst (10% Pd/C) is added. It is hydrogenated for 12 hours at room temperature. The catalyst is filtered out, and the filtrate is evaporated to dryness in a vacuum.

Yield: 5.96 g (quantitative) of a slightly cream-colored solid

Analysis:

Cld: C 57.34 H 10.83 N 22.29

Fnd: C 57.28 H 10.90 N 22.19 d) 1,7-Di[4,7,10-tris(carboxymethyl)-1,4,7,10-tetraazacyclododecan-1-yl]-2,6-dimethoxy-4-oxaheptane 5.8 g (11.54 mmol) of the title compound of Example 9c is dissolved in 100 ml of water and 16.03 g (115.4 mmol) of bromoacetic acid is added. The pH is brought to 9.5 with 6 N potassium hydroxide solution. It is heated to 60° C. and the pH is kept between 9.5–10 by adding 6 N potassium hydroxide solution. After 24 hours of stirring at 60° C., it is cooled in an ice bath, adjusted to pH 1 with concentrated hydrochloric acid and evaporated to dryness in a vacuum. The residue is dissolved in a little water and put on a cation-exchange column (IR 120). After flushing with water, the ligand is eluted with 0.5 N ammonia-water solution. The fractions are concentrated by evaporation, the ammonium salt is taken up with a little water and put on an anion-exchange column (IRA 67). It is washed first with water and then eluted with 0.5 N aqueous formic acid. It is concentrated by evaporation in a vacuum, the residue is dissolved in a little hot ethanol and acetone is added. After cooling in an ice bath, the title compound crystallizes out.

Yield: 6.65 (61% of theory) of a hygroscopic solid

Water content: 10.1%

Analysis (relative to anhydrous substance):

Cld: C 50.81 H 7.82 N 13.17

Fnd: C 50.74 H 7.85 N 13.05 e) Bis europium complex of 1,7-di[4,7,10-tris(carboxymethyl)-1,4,7,10-tetraazacyclododecan-1-yl]-2,6-dimethoxy-4-oxaheptane 6.5 g (7.638 mmol) of the title compound of Example 9d is dissolved in 50 ml of water and 2.68 g (7.638 mmol) of europium oxide is added. It is stirred for 3 hours at 90° C. The solution is stirred for one hour with 2 ml of acidic ion exchanger (AMB 252c/H$^+$ form) and 2 ml of weakly basic exchanger (IRA 67/OH-form) at room temperature. Exchanger is filtered out, and the filtrate is freeze-dried.

Yield: 9.26 g (98% of theory) of a vitreous solid.

Water content: 7.2%

Analysis (relative to anhydrous substance):

Cld: C 37.64 H 5.26 N 9.75 Eu 26.45

Fnd: C 37.53 H 5.30 N 9.70 Eu 26.35

EXAMPLE 10

For selected complexes, in vitro measurements that were suitable for determining various parameters significant for temperature measurement were made. To this end, a 0.01 molar aqueous solution was produced from the respective complex and measured at various temperatures in the range between 46° C. and 26° C. The intense signal of the solvent ($H_2O$) was suppressed by selective pre-saturation and by the use of narrow-band audio filters. The results of these studies are summarized in FIG. 3/3.

EXAMPLE 11 a) 4-($\alpha,\alpha,\alpha$-Tris(hydroxymethyl)-methyl)-1,7-bis(p-tolylsulfonyl)-1,4,7-triazaheptane 143.3 g (726 mmol) of tosylaziridine is added to 40 g (330 mmol) of tris-(hydroxymethyl)-methylamine, dissolved in a mixture of ethanol/water/acetonitrile (200/50/200 ml) and stirred for 2 days at 45° C. It is evaporated to dryness and the residue is chromatographed on silica gel (mobile solvent: methylene chloride/ethanol 15:1).

Yield: 97 g (57% of theory) of a vitreous solid

Elementary analysis:

Cld: C 51.24 H 6.45 N 8.15

Fnd: C 51.41 H 6.55 N 8.02 b) 1-(($\alpha,\alpha,\alpha$-Tris(hydroxymethyl)-methyl)-4,7,10-tris(p-tolylsulfonyl)-1,4,7,10-tetraazacyclododecane 95 g (184.2 mmol) of the title compound of Example 11a) is dissolved in 900 ml of dimethylformamide and 24.31 g (1013 mmol) of sodium hydride is added. It is stirred for 2 hours at room temperature, then it is heated to 100° C. 104.6 g (184.2 mmol) of N-bis[2-(4-methylphenylsulfonyloxy)-ethyl]-4-methyl-phenylsulfonamide, dissolved in 700 ml of dimethylformamide, is instilled in this solution over 3 hours and then stirred overnight at 100° C. It is evaporated to dryness in a vacuum, the residue is taken up in 2000 ml of water and extracted 5 times with 300 ml of methylene chloride each. The organic phase is dried on magnesium sulfate and evaporated to dryness. The residue is chromatographed on silica gel (mobile solvent =methylene chloride/ethanol 20:1).

Yield: 50.36 g (37% of theory) of a cream-colored solid

Elementary analysis:

Cld: C 53.64 H 6.27 N 7.58 S 13.02

Fnd: C 53.75 H 6.38 N 7.49 S 12.87 c) 1-($\alpha,\alpha,\alpha$-Tris(methoxymethyl)-methyl)-4,7,10-tris(p-tolylsulfonyl)-1,4,7,10-tetraazacyclododecane 50 g (67.66 mmol) of the title compound of Example 11b) is dissolved in 500 ml of dimethylformamide and 6.5 g (270.64 mmol) of sodium hydride is added. It is stirred for 6 hours at room temperature. Then, 38.4 g (270.64 mol) of iodomethane, dissolved in 100 ml of dimethylformamide, is instilled over 30 minutes and then stirred overnight at 50° C. 2000 ml of ice water is carefully added and extracted 3 times with 300 ml of ethyl acetate. The organic phase is shaken out twice with 10% common salt solution and then dried on magnesium sulfate. After concentration by evaporation of the organic phase in a vacuum, the residue is chromatographed on silica gel (mobile solvent =methylene chloride/acetone 15:1).

Yield: 47.56 g (90% of theory) of a colorless solid

Elementary analysis:

Cld: C 55.36 H 6.71 N 7.17 S 18.44

Fnd: C 55.43 H 6.80 N 7.05 S 18.30 d) 1-($\alpha,\alpha,\alpha$-Tris(methoxymethyl)-methyl)-1,4,7,10-tetraazacyclododecane 39.75 g (1.73 mol) of sodium is added in portions to 45 g (57.62 mmol) of the title compound of Example 11c) in 1000 ml of n-butanol at 100° C. and it is stirred overnight at this temperature. It is cooled to room temperature, and 1000 ml of 20% common salt solution is added. The organic phase is separated and evaporated to dryness in a vacuum. The residue is chromatographed on silica gel (mobile solvent= ethanol/25% ammonia-water solution 10:1).

Yield: 12.29 g (67% of theory) of a pale yellow oil, which solidifies with standing Water content: 5.1%

Elementary analysis (relative to anhydrous substance):

Cld: C 56.57 H 10.76 N 17.59

Fnd: C 56.40 H 10.85 N 17.43 e) 1-($\alpha,\alpha,\alpha$-Tris(methoxymethyl)-methyl)-4,7,10-tris (carboxymethyl)-1,4,7,10-tetraazacyclododecane 12 g (37.68 mmol) of the title compound of Example 11d) is dissolved in 200 ml of water and 26.2 g (188.4 mmol) of bromoacetic acid is added. The pH is brought to 9.5 with 6 N potassium hydroxide solution. It is heated to 60° C. and the pH is kept between 9.5–10 by adding 6 N potassium hydroxide solution. After 24 hours of stirring at 60° C., it is cooled in an ice bath, adjusted with concentrated hydrochloric acid to pH 1 and evaporated to dryness. The residue is put on a cation-exchange column (IR 120/H$^+$ form). After flushing with water, the ligand is eluted with 0.5 N aqueous ammonia solution. The fractions are concentrated by evaporation and put on an anion-exchange column (IRA 67/OH$^-$ form). It is washed with water and then eluted with 0.5 N formic acid. It is evaporated to dryness in a vacuum, the residue is dissolved in a little hot methanol and acetone is added. After cooling in an ice bath, the title compound crystallizes out.

Yield: 13.17 g (71% of theory) of a vitreous solid

Water content: 9.3%

Elementary analysis (relative to anhydrous substance):

Cld: C 51.21 H 8.18 N 11.37

Fnd: C 51.13 H 8.31 N 11.24 f) Praseodymium complex of 1-($\alpha,\alpha,\alpha$-tris(methoxymethyl)-methyl)-4,7,10-tris(carboxymethyl)-1,4,7,10-tetraazacyclododecane 4 g (8.12 mol) of the title compound of Example 11e) is dissolved in 40 ml of water and 1.34 g (4.06 mol) of praseodymium oxide is added. It is stirred for 3 hours at 90° C. The solution is stirred for one hour with 5 ml of acidic ion exchanger (AMB 252c/H$^+$ form) and 5 ml of weakly basic exchanger (IRA 67/OH$^-$ form) at room temperature. Exchanger is filtered out, and it is freeze-dried.

Yield: 5.07 g (99% of theory) of a vitreous solid

Water content: 10.1%

Elementary analysis (relative to anhydrous substance):

Cld: C 40.01 H 5.92 N 8.89 Pr 22.35

Fnd: C 39.87 H 6.03 N 8.73 Pr 22.21 g) Europium complex of 1-($\alpha,\alpha,\alpha$-tris(methoxymethyl)-methyl)-4,7,10-tris (carboxymethyl) -1,4,7,10-tetraazacyclododecane 4 g (8.12 mmol) of the title compound of Example 11e) is dissolved in 40 ml of water and 1.43 g (4.06 mol) of europium oxide is added. It is stirred for 3 hours at 90° C. The solution is stirred for one hour with 5 ml of acidic ion exchanger (AMB 252c/H$^+$ form) and 5 ml of weakly basic exchanger (IRA 67/OH$^-$ form) at room temperature. Exchanger is filtered out, and it is freeze-dried.

Yield: 5.10 g (98% of theory) of a vitreous solid

Water content: 9.7%

Elementary analysis (relative to anhydrous substance):

Cld: C 39.32 H 5.81 N 8.73 Eu 23.69

Fnd: C 39.25 H 5.96 N 8.61 Eu 23.55 h) Dysprosium complex of 1-($\alpha,\alpha,\alpha$-tris(methoxymethyl)-methyl)-4,7,10-tris(carboxymethyl)-1,4,7,10-tetraazacyclododecane 4 g (8.12 mmol) of the title compound of Example 11e) is dissolved in 40 ml of water and 1.43 g (4.06 mol) of dysprosium oxide is added. It is stirred for 3 hours at 90° C. The solution is stirred for one hour with 5 ml of acidic ion exchanger (AMB 252c/H$^+$ form) and 5 ml of weakly basic exchanger (IRA 67/OH$^-$ form) at room temperature. Exchanger is filtered out, and it is freeze-dried.

Yield: 5.24 g (99% of theory) of a vitreous solid

Water content: 8.9%

Elementary analysis (relative to anhydrous substance):

Cld: C 38.68 H 5.72 N 8.59 Dy 24.92

Fnd: C 38.51 H 5.83 N 8.47 Dy 24.81

EXAMPLE 12 a) 10-(3,6-Dioxa-heptyl)-1,4,7-tris-(carboxymethyl)-1,4,7,10-tetraazacyclododecane 3 g (8.66 mmol) of 1,4,7-tris-(carboxymethyl)-1,4,7,10-tetraazacyclododecane is stirred in 50 ml of dimethylformamide for 10 hours with 1.83 g (10 mmol) of 1-bromo- 3,6-dioxa-heptane, 100 mg of sodium iodide and 4 g of potassium carbonate at 90° C. It is concentrated by evaporation in a vacuum and the residue is spread between 100 ml of water and 50 ml of diethyl ether. The aqueous phase is adjusted to pH 2 with 5 N hydrochloric acid and evaporated to dryness. The residue is refluxed with 200 ml of methanol, the undissolved material is filtered out, evaporated to dryness in a vacuum, the residue is dissolved in 50 ml of water, adjusted to pH 2 with 5 N hydrochloric acid and the solution is put on a column with 200 ml of cation exchanger IRC 50. It is eluted first with 0.5 l of water, which is discarded. Then, it is eluted with 0.5 l of 0.5 N ammonia solution. It is evaporated almost to dryness in a vacuum, mixed with 100 ml of water and enough cation exchanger IRC 50 is added with stirring to reach pH 3.5. The solution is then filtered and freeze-dried. 2.95 g of the title compound with a water content of 3.5% is obtained.

Elementary analysis (relative to anhydrous substance):

Cld: C 50.88 H 8.09 N 12.49

Fnd: C 50.92 H 7.81 N 12.32 b) Praseodymium complex of 10-(3,6-dioxa-heptyl)-1,4,7-tris-(carboxymethyl)-1,4,7,10-tetraazacyclododecane 2.50 g (5.57 mmol, relative to anhydrous substance) of the title compound of Example 12a) is stirred in 30 ml of water with 919 mg of praseodymium oxide for 4 hours at 85° C. It is cooled to room temperature, filtered, and the solution is stirred for one hour with 1.5 ml of acidic ion exchanger (AMB 252c, $H^+$ form) and 1.5 ml of basic ion exchanger (IRA 67, $OH^-$ form). It is filtered, freeze-dried and 2.85 g of the light green title compound with a water content of 5.05% is obtained.

Elementary analysis (relative to anhydrous substance):

Cld: C 38.92 H 5.67 N 9.55 Pr 24.03

Fnd: C 38.69 H 5.91 N 9.71 Pr 23.89 c) Dysprosium complex of 10-(3,6-Dioxa-heptyl)-1,4,7-tris-(carboxymethyl)-1,4,7,10-tetraazacyclododecane Analogously to Example 12b), dysprosium oxide instead of praseodymium oxide is used. 3 g of the title compound with a water content of 4.5% is obtained.

Elementary analysis (relative to anhydrous substance):

Cld: C 37.53 H 5.47 Dy 26.73 N 9.22

Fnd: C 37.71 H 5.70 Dy 26.59 N 9.38

EXAMPLE 13

Purpose of the Study:

In vivo temperature measurement on the anesthetized animal after i.v. administration of the compound produced according to Example 6c) with $^1H$ magnetic resonance spectroscopy (MRS). Comparison of the measurement results with the measured values of a comparison measurement with a temperature sensor.

Procedure:

Hardware: Electric temperature sensor OTD 85, Ellab Company Nuclear spin tomograph: SIS 85/310, SISCO Company, 2 Tesla magnet, Oxford Company.

For the $^1H$-MRS, a surface coil with ø 20 mm was placed in the liver area of the animal. Spectra with 3 X water suppression and excitation with frequency-selective gaussian pulse (4 ms) with nt=1000 and TR=0.25 sec were recorded.

Animal: Wistar Han rat, 150 g, n=3.

Substance: Compound produced according to Example 6c), aqueous solution, 500 mmol/L, pH 7.4.

Dose: 0.75 to 1 mmol/kg i.v. The animals were anesthetized (Rompun-Ketavet) at the beginning of the study.

Then, their body temperatures dropped considerably. In the nuclear spin tomographs, the animals were placed on a water bed, which was initially left at room temperature. There was a waiting period until a constant temperature was established, which was measured rectally with a temperature sensor. Then, the first dose of compound 6c) was administered and 6 spectra at 4.3 minutes apiece were recorded in succession. Then, the rectal temperature was measured again, then the water bed was heated to 41° C., and again there was a waiting period until a constant rectal temperature was established in the animal. The rectal temperature increased during this heating by about 2°–3° C. After administration of a second dose of compound 6c) (the first dose had already been eliminated renally), 6 spectra at 4.3 minutes apiece were recorded again. Then, the rectal temperature was measured again.

The evaluation of the spectra was done by determination of the chemical shift of the measurement signal from the water signal, which was used as reference. The conversion of the chemical shift of the measurement signal to temperature was done by means of a calibration curve, which was recorded in bovine plasma at a concentration of 2.5 mmol/L of compound 6c) and which reflects as precisely as possibly the in vivo conditions.

Result:

In the table, the results of the measurement of the body temperatures of the three animals studied are summarized. The first column indicates mean value ±1 standard deviation of the measurement with the temperature sensor before and after spectroscopy. The measured values of 6 spectra were averaged, and the difference between them and the results from the thermosensor is indicated in the second column. The standard deviation of the 6 $^1H$-MRS measured values are indicated in the third column and are used as a yardstick for the reproducibility of the measuring process.

|  | Temperature sensor, rectal (n = 2) [°C.] | Measuring difference between $^1H$-MRS and the temperature sensor [°C.] | Reproducibility of $^1H$-MRS (n = 6) [°C.] |
|---|---|---|---|
| animal, anesthesia |  |  |  |
| 1 | 31.5 ± 0.0 | +2.3 | ±0.4 |
| 2 | 29.9 ± 0.7 | +0.5 | ±0.6 |
| 3 | 30.3 ± 0.4 | −1.1 | ±0.3 |
| animal, anesthesia + heated |  |  |  |
| 1 | 34.5 ± 0.1 | 0 | ±0.2 |
| 2 | 31.6 ± 0.7 | +1.4 | ±0.4 |
| 3 | 33.3 ± 0.6 | −0.6 | ±0.3 |

In the case of the anesthetized animals, with one exception, a good correspondence (deviation<1.5° C.) between the measured values of the temperature sensor and $^1H$-MRS was found. In this case, it can be taken into consideration that the temperatures that are measured by the two methods do not necessarily have to correspond exactly since they are measured in different areas of the body (temperature sensor rectally and spectroscopy in the liver area). The reproducibility of the 6 spectra respectively in one animal was good (about ±0.5° C.). The dose of 0.75 to 1 mmol/kg is sufficient with a measurement by the surface coil (about 5 ml of detected measured volume) to record several spectra with informative values over a period of about 30–45 minutes p.a.

Conclusion:

With compound 6c), a temperature difference of 1°–2° C. can be depicted in a limited volume with sufficient reliability (±0.5° C.). The measuring period for an individual spectrum is about 5 minutes.

Bibliography:

(1) R. Duerst et al., Rev. Sci. Instrum. 36 (1965) 1896, F. Conti, Rev. Sci. Instrum. 38 (1967) 128, A. L. Van Geet, Anal. Chem. 40 (1968) 2227, A. L. Van Geet, Anal. Chem. 42 (1970) 678, C. Ammann et al., J. Magn. Reson. 46 (1982) 319;

(2) D. R. Vidrin et al., Anal. Chem. 48 (1976) 1301;

(3) R. K. Gupta et al., J. Magn. Reson. 40 (1980)587;

(4) J. T. Bailey et al., J. Magn. Reson. 37 (1980) 353;

(5) P. E. Peterson, Anal. Chem. 50 (1978) 298;

(6) B. A. Berkowitz et al., NMR in Biomedicine 5 (1992) 65;

(7) M. J. Foster et al., J. Magn. Reson. 65 (1985) 497;

(8) K. Roth, Magn. Reson. Chem. 25 (1987) 429

(9) EP 0 095 124.

We claim:

1. A method for determining temperature which comprises determining the change in chemical shift of a complex subject to NMR spectroscopy, wherein the complex is a macrocyclic metal complex of at least one metal ion of an element of atomic numbers 21–29, 42, 44 or 57–70 and a complexing agent of formula I in which n means the numbers 0 or 1, $R^1$ independently of one another, stand for a hydrogen atom or a metal ion equivalent, $R^3$ stands for a hydrogen atom, a straight-chain or branched $C_1$–$C_{10}$ alkyl group, which is optionally substituted by 1–5 $C_1$–$C_6$ alkoxy groups, hydroxy-$C_1$–$C_6$ alkyl groups and/or hydroxy groups, $R^2$ means a straight-chain or branched $C_1$–$C_{10}$ alkylene group, which optionally is interrupted by 1 to 5 oxygen atoms and/or carbonyl groups and/or optionally is substituted by 1 to 5 hydroxy groups, $C_1$–$C_6$ alkoxy-$C_1$–$C_6$ alkyl groups, —$OR^4$, —CO—$NR^5R^6$, —$NR^5R^6$ and/or —$NR^5$—CO—$R^6$ radicals, in which $R^4$ stands for a straight-chain or branched $C_1$–$C_4$ alkyl radical and $R^5$, $R^6$, independently of one another, have the meaning of $R^3$, and A stands for a hydrogen atom or a second macrocyclic radical of general formula II, in which n, $R^1$ and $R^3$ have the indicated meanings, where free carboxylic acid groups that are not required for complexing a metal ion are present optionally as a salt of an inorganic or organic base or amino acid and/or as an ester or amide and where at least two radicals $R^1$ stand for a metal ion equivalent.

2. The method of claim 1, wherein the macrocyclic metal complex contains, as radical $R^2$—A, a —$CH_2CH_2OCH_3$, —$CH_2CH_2O$—$C(CH_3)_3$, —$CH_2$—$CH(OH)$—$CH_2OCH_3$, —$CH_2CH(OH)$—$CH_2O$—$CH(CH_3)_2$, —$CH_2$—$CH(OH)$—$CH_2O$—$C(CH_3)_3$, —$CH_2$—$CH(OH)$—$CH_3$, —CH($CH_2OCH_3)_2$, —$CH(CH_2OCH_3)$—$CH(OH)CH_2OH$, —$CH_2$—$CH_2$—NH—$CH_3$, —$CH_2$—$CH_2$—$N(CH_3)_2$, —$CH_2$—CO—$N(CH_3)_2$, —$CH_2$—$CH_2$—O—$CH_2$—$Ch_2$—O—$Ch_3$, or —$C(CH_2OCH_3)_3$ group.

3. The method of claim 1, wherein the macrocyclic metal complex is a praseodymium complex of 10-(3-oxabutyl)-1,4,7-tris-(carboxymethyl)-1,4,7,10-tetraazacyclododecane.

4. The method of claim 1, wherein the macrocyclic metal complex is a europium complex of 10-(3-oxabutyl)-1,4,7-tris-(carboxymethyl)-1,4,7,10-tetraazacyclo-dodecane.

5. The method of claim 1, wherein the change of chemical shift of at least two different macrocyclic metal complexes is determined, wherein the chemical shift of one complex exhibits a negative temperature gradient and the chemical shift of another complex exhibits a positive temperature gradient.

6. The method of claim 1, wherein the radical $R^2$—A is —$CH_2CH_2OCH_3$ or —$CH_2CH_2OC(CH_3)_3$.

7. The method of claim 1, wherein the change in chemical shift is independent of ionic strength, pH or oxygen partial pressure.

8. The method of claim 1, wherein at least one metal ion is a paramagnetic metal ion.

9. The method of claim 1, wherein at least one metal ion is a lanthanoid element ion.

10. The method of claim 1, wherein the complex is administered to a patient and the temperature is determined in vivo.

11. The method of claim 10, wherein the complex is administered in a dose of 0.005–20 mmol/kg body weight.

12. The method of claim 10, wherein the temperature in a body tissue is determined.

13. The method of claim 1, wherein the temperature is determined within an error range of ±0.5° C.

14. The method of claim 1, wherein the measuring period for a single spectrum is about 5 minutes or less.

15. A method for determining temperature in a body tissue in vivo which comprises measuring the change in chemical shift by NMR spectroscopy of a complex in or on the tissue wherein the complex is at least one metal ion of an element of atomic numbers 21–29, 42, 44 or 57–70 and a complexing agent of formula I in which n means the numbers 0 or 1,

R$^1$ independently of one another, stand for a hydrogen atom or a metal ion equivalent, R$^3$ stands for a hydrogen atom, a straight-chain or branched C$_1$–C$_{10}$ alkyl group, which is optionally substituted by 1–5 C$_1$–C$_6$ alkoxy groups, hydroxy-C$_1$–C$_6$ alkyl groups and/or hydroxy groups, R$^2$ means a straight-chain or branched C$_1$–C$_{10}$ alkylene group, which optionally is interrupted by 1 to 5 oxygen atoms and/or carbonyl groups and/or optionally is substituted by 1 to 5 hydroxy groups, C$_1$–C$_6$ alkoxy-C$_1$–C$_6$ alkyl groups, —OR$^4$, —CO—NR$^5$R$^6$, —NR$^5$R$^6$ and/or —NR$^5$—CO—R$^6$ radicals, in which R$^4$ stands for a straight-chain or branched C$_1$–C$_4$ alkyl radical and R$^5$, R$^6$, independently of one another, have the meaning of R$^3$, and A stands for a hydrogen atom or a second macrocyclic radical of general formula II, in which n, R$^1$ and R$^3$ have the indicated meanings, where free carboxylic acid groups that are not required for complexing a metal ion are present optionally as a salt of an inorganic or organic base or amino acid and/or as an ester or amide and where at least two radicals R$^1$ stand for a metal ion equivalent.

16. The method of claim 15, further comprising administering the complex in a dose of 0.005–20 mmol/kg body weight.

17. The method of claim 15, wherein the macrocyclic metal complex contains, as radical R$^2$—A, a —CH$_2$CH$_2$OCH$_3$, —CH$_2$CH$_2$O—C(CH$_3$)$_3$, —CH$_2$—CH(OH)—CH$_2$OCH$_3$, —CH$_2$CH(OH)—CH$_2$O—CH(CH$_3$)$_2$, —CH$_2$—CH(OH)—CH$_2$O—C(CH$_3$)$_3$, —CH$_2$—CH(OH)—CH$_3$, —CH(CH$_2$OCH$_3$)$_2$, —CH(CH$_2$OCH$_3$)—CH(OH)CH$_2$OH, —CH$_2$—CH$_2$—NH—CH$_3$, —CH$_2$—CH$_2$—N(CH$_3$)$_2$, —CH$_2$—CO—N(CH$_3$)$_2$, —CH$_2$—CH$_2$—O—CH$_2$—Ch$_2$—O—Ch$_3$, or —C(CH$_2$OCH$_3$)$_3$ group.

18. The method of claim 15, wherein the macrocyclic metal complex is a praseodymium complex of 10-(3-oxabutyl)-1,4,7-tris-(carboxymethyl)-1,4,7,10-tetraazacyclododecane.

19. The method of claim 15, wherein the macrocyclic metal complex is a europium complex of 10-(3-oxabutyl)-1,4,7-tris-(carboxymethyl)-1,4,7,10-tetraazacyclododecane.

20. The method of claim 15, wherein the change of chemical shift of at least two different macrocyclic metal complexes is determined, wherein the chemical shift of one complex exhibits a negative temperature gradient and the chemical shift of another complex exhibits a positive temperature gradient.

21. The method of claim 15, wherein the radical R$^2$—A is —CH$_2$CH$_2$OCH$_3$ or —CH$_2$CH$_2$OC(CH$_3$)$_3$.

22. The method of claim 15, wherein the change in chemical shift is independent of ionic strength, pH or oxygen partial pressure.

23. The method of claim 15, wherein at least one metal ion is a paramagnetic metal ion.

24. The method of claim 15, wherein at least one metal ion is a lanthanoid element ion.

25. The method of claim 15, wherein the temperature in a body tissue is determined.

26. The method of claim 15, wherein the temperature is determined within an error range of ±0.5° C.

27. The method of claim 15, wherein the measuring period for a single spectrum is about 5 minutes or less.

* * * * *